United States Patent [19]

Kitsuki et al.

[11] Patent Number: 5,196,601
[45] Date of Patent: Mar. 23, 1993

[54] PROCESS FOR PRODUCING ALCOHOL OR AMINE

[75] Inventors: Tomohito Kitsuki, Wakayama; Yoshiaki Fujikura, Utsunomiya, both of Japan

[73] Assignee: Kao Corporation, Tokyo, Japan

[21] Appl. No.: 899,951

[22] Filed: Jun. 17, 1992

Related U.S. Application Data

[63] Continuation of Ser. No. 630,230, Dec. 19, 1990, abandoned.

[30] Foreign Application Priority Data

Dec. 26, 1989 [JP] Japan .................................. 1-337227

[51] Int. Cl.$^5$ ...................... C07C 29/32; C07C 27/04; C07C 209/30
[52] U.S. Cl. ................... 568/817; 564/373; 564/385; 564/414; 564/415; 564/416; 564/472; 564/473; 564/488; 564/489; 564/490; 564/494; 568/814; 568/816; 568/819; 568/820; 568/861; 568/862; 568/864; 568/867; 568/880; 568/884
[58] Field of Search ............... 564/373, 385, 414, 415, 564/416, 472, 473, 488, 489, 490, 494; 568/814, 816, 819, 820, 817, 861, 862, 864, 867, 880, 884

[56] References Cited

U.S. PATENT DOCUMENTS

| | | | |
|---|---|---|---|
| 4,837,367 | 6/1989 | Gustafson et al. | 568/862 |
| 4,839,340 | 6/1989 | Fujikura et al. | 568/820 |
| 4,912,265 | 3/1990 | Franklin | 568/814 |
| 4,943,652 | 7/1990 | Yatagai et al. | 568/814 |
| 5,023,379 | 7/1991 | Felder et al. | 564/472 |

FOREIGN PATENT DOCUMENTS

| | | | |
|---|---|---|---|
| 0746669 | 7/1970 | Belgium | 564/385 |
| 0070566 | 1/1983 | European Pat. Off. | 568/820 |
| 2751383 | 5/1978 | Fed. Rep. of Germany | 568/867 |
| 0019903 | 2/1979 | Japan | 564/385 |

*Primary Examiner*—Werren B. Lone
*Attorney, Agent, or Firm*—Oblon, Spivak, McClelland, Maier & Neustadt

[57] ABSTRACT

Disclosed herein is a process for producing an alcohol or an amine by reducing a compound having a formyl, keto, nitro, oxirane, ester, nitrile, amide or halogenated carboxyl group with an alkali metal boro-hydride in the presence of a compound having a hydroxyl group and ether linkage. According to the present invention, a functional group having a great steric hindrance can be reduced, and a corresponding alcohol or amine can efficiently be produced under very mild conditions on an industrial scale.

5 Claims, No Drawings

PROCESS FOR PRODUCING ALCOHOL OR AMINE

This application is a continuation of application Ser. No. 07/630,230, filed on Dec. 19, 1990, now abandoned.

BACKGROUND OF THE INVENTION

1) Field of the Invention

The present invention relates to a process for efficiently producing an alcohol or an amine.

2) Description of the Background Art

Conventional approaches for reducing organic functional groups include reduction using a metal hydride such as lithium aluminum hydride or sodium borohydride and hydrogenation using a transition metal catalyst such as platinum oxide, ruthenium carried by activated carbon or Cu-Cr catalyst.

However, these approaches have at least one of the following problems.

(1) A severe reaction condition such as high temperature/high pressure is required.

(2) Only limited functional groups can be reduced.

(3) If applied to a functional group having a great steric hindrance, the yield of the product is low.

(4) The reducing agent is sometimes not readily available because it is not industrially produced. Moreover, even when industrially produced, it is instable to the moisture contained in the atmosphere or in the reaction system and therefore is not free from the danger of ignition.

For example, when organic functional groups are reduced without using any transition metal catalyst, the use of lithium aluminum hydride is accompanied by the danger of ignition because it is very instable to the moisture contained in the reaction system or in the atmosphere. In this respect, sodium borohydride is suitable for the industrial use because it is stable against the moisture contained in the reaction system or in the atmosphere. This approach of using sodium borohydride alone, however, has only limited applications: Aldehydes, ketones and acid chlorodies are successfully reduced; oxiranes, esters and lactones are reduced at a very slow reaction speed; carboxylates, tertiary amides and nitriles cannot be reduced.

Further, in order to improve the reducing ability of sodium borohydride, several approaches have been proposed, which include a method of effectively reducing esters, lactones or oxiranes by having a sodium borohydride and a lithium halogenide coexist and converting the sodium borohydride into lithium borohydride in the system (Tetrahedron vol. 35, p567–607 (1979)) and a method of reducing acid amides, nitriles or carboxylic acids by making a carboxylic acid react on a sodium borohydride and converting it into an acylated sodium borohydride (Journal of Organic Synthetic Chemistry Association, 35(4), 300–303, 1977). It has also been reported that tertiary and primary amides can be reduced by using pyridine as a solvent. Recently, it has been reported that a method of using tetrahydrofuran, diglyme (diethylene glycol dimethyl ether), t-butanol or the like as a solvent and adding methanol dropwise to the system can successfully reduce esters, lactones, oxiranes and disulfides in the presence of sodium borohydride (Bull. Chem. Soc. Jpn., 57, 1948–1953 (1984)), and nitriles, nitro compounds, primary amides and carboxylic acids can be reduced in the presence of lithium borohydride (J. Chem. Soc., Chem. Commun., 668 (1983), J. Org. Chem., 51, 4000 (1986)).

However, lithium borohydride is not industrially supplied, and for obtaining it from sodium borohydride and a lithium halogenide, a large amount of expensive lithium salt is required. Moreover, an acylated sodium borohydride may be deactivated when certain solvents are used. Any one of the above methods of reducing amides requires a large amount of sodium borohydride, and at least five times the molar amount of the substrate. Besides, tertiary amides and nitriles can be reduced only in low yields and esters cannot be reduced at all. On the other hand, when sodium borohydride itself is used, nitriles, nitro compounds, amides and carboxylic acids cannot be reduced even by the method of using tetrahydrofuran, diglyme, t-butanol or the like as a solvent and adding methanol dropwise to the reaction system. Moreover, a large amount of solvent and methanol is required for the reduction of esters, lactones and oxiranes, which means very low industrial productivity. The method of using sodium borohydride and a solvent pyridine has some drawbacks; secondary amides cannot be reduced; tertiary amides can be reduced but yield is low; nitriles are byproduced from primary amides.

Turning to the hydrogenation reaction which proceeds in the presence of a transition metal catalyst, it is an economical process but was found to have the following problem: When applied to compounds having keto groups which have a great steric hindrance, the reaction stops at an equilibrium state where a large residual amount of ketone is left and the conversion cannot proceed even under conditions of high temperature, high hydrogen pressure, and a use of any one of platinum oxide, ruthenium carried by activated carbon or Cu-Cr catalyst. That is to say, for a compound having a functional group of a great steric hindrance, this method could not lead to a satisfactory yield.

For example, the present inventors disclosed a method of producing bornane-3-spiro-1'-cyclopentane-2-ol (III), which is a very useful compound as an odorant substance, by reducing bornane-3-spiro-1'-cyclopentane-2-one (II) with hydrogen by the use of ruthenium carried by activated carbon as a catalyst (Japanese Patent Application Kokai No. 121,938/1990). However, when the ketone (II) was reduced under the condition of high temperature and high hydrogen pressure by the use of this catalyst, the reaction stopped at an equilibrim state where a large amount of the ketone (II) was left and the conversion rate could not be successfully enhanced.

If a lithium aluminum hydride is used, bornane-3-spiro-1'-cyclopentane-2-one can be quantitatively reduced. However, to carry out this reduction on an industrial scale, a special care is needed in handling this reagent because it is very sensitive to the moisture, and the solvent must be strictly purified. Thus, this method is not a simple and economical one. In contrast, use of alkali metal borohydride, whose handling is not so restricted compared to lithium aluminum hydride, is accompanied by a drawback in that when applied to bornane-3-spiro-1'-cyclopentane-2-one (II), and when a lower alcohol, diethyl ether or tetrahydrofuran is used as a solvent, the yield is very low or the reaction does not proceed at all. It is inferred that this ketone compound (II) is difficult to be reduced because of the steric hindrance of the carbonyl group. Recently, in order to improve the reducing ability, a modified process has been developed, where a solvent mixture system of an ether solvent such as tetrahydrofuran-methanol or the like and a lower alcohol is utilized (Bull, Chem. Soc. Jpn., 57, 1948-1953 (1984)). However, sodium borohydride in an amount at least 2.5 times the amount of the substrate and a large amount of a solvent at least 10 times the volume of the substrate are required to complete the reaction by this method. Thus, implementation of this method on an industrial scale is not advisable in terms of the productivity and economy.

SUMMARY OF THE INVENTION

Under these circumstances, the present inventors made intensive studies and, as a result, found that a functional group, even when it had a great steric hindrance, could be successfully reduced and a corresponding alcohol or amine could efficiently be produced under a very mild condition on an industrial scale by reducing a compound having a functional group with an alkali metal borohydride in the presence of a compound having a hydroxyl group and ether linkage.

Accordingly, the present invention provides a process for producing an alcohol or an amine which comprises reducing a compound having formyl, keto, nitro, oxirane, ester, nitrile, amide, carboxyl or halogenated carboxyl groups with an alkali metal borohydride in the presence of a compound having a hydroxyl group and ether linkage. The above and other object, features and advantages of the present invention will become apparent from the following description.

DETAILED DESCRIPTION OF THE INVENTION AND PREFERRED EMBODIMENTS

In the present invention, compounds to be reduced which have formyl groups are not specially restricted, and include benzaldehyde, citronellal, hydrotropaldehyde, lyral and the like. The corresponding alcohols can be produced by reducing these compounds.

Compunds having keto groups to be reduced according to this invention are not specially restricted, and include methylheptenone, carvone, camphor, bornane-3-spiro-1'-cyclopentane-2-one, benzophenone, muscone and the like. The corresponding alcohols can be produced by reducing these compounds.

Compounds having nitro groups to be reduced according to this invention are not specially restricted, and include nitrobenzene, nitropropane, musk ambrette and the like. The corresponding amines can be produced by reducing these compounds.

Compounds having oxirane groups to be reduced according to this invention are not specially restricted, and include styrene oxide, stilbene oxide, cyclohexene oxide, α-pinene oxide and the like. The corresponding alcohols can be produced by reducing these compounds.

Compounds having ester groups to be reduced according to this invention are not specially restricted, and include methyl benzoate, linaryl acetate, cedryl acetate, bornyl acetate, α, ω-dimethyl pentadecanoate, cyclopentadecanolide and the like. The corresponding alcohols can be produced by reducing these compounds.

Compounds having nitrile groups to be reduced according to this invention are not specially restricted, and include geranyl nitrile, citronellylnitrile, benznitrile and the like. The corresponding amines can be produced by reducing these compounds.

Compounds having amide groups to be reduced according to this invention are not specially restricted, and include benzamide, N-methyl benzamide, N,N-dimethyl benzamide and the like. The corresponding amines can be produced by reducing these compounds.

Compounds having carboxyl groups to be reduced according to this invention are not specially restricted, and include caproic acid, benzoic acid, α, ω-pentadecanoic acid, phthalic anhydride and the like. Examples of the compounds having halogenated carboxyl groups, which are not specially restricted, include caproic acid chloride, benzoic acid chloride, α, ω-pentadecanoic acid chloride and the like. The corresponding alcohols can be produced by reducing these compounds.

The present invention can also be applied to the reduction of disulfides. Examples of the difulfides include diaryl sulfides and diphenyl disulfide and the corresponding thiols can be produced by reducing these compounds.

The compounds used in the present invention, which have a hydroxyl group and an ether linkage (hereinafter referred to as a hydroxyl ether compound), are represented by the following formula (I):

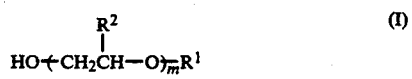

wherein $R^1$ represents an alkyl group or an alkenyl group; $R^2$ represents a hydrogen atom or an alkyl group; $R^1$ and $R^2$ may be linked together to form an alkylene group; and m represents a number of 1 to 5.

Typical compounds of formula (I) are ethylene glycol monoalkyl ethers, diethylene glycol monoalkyl ethers, triethylene glycol monoalkyl ethers and cyclic ether alcohols, and in particular ethylene glycol monoethyl ether, ethylene glycol monobutyl ether, diethylene glycol monoethyl ether, diethylene glycol monobutyl ether, triethylene glycol monoethyl ether, triethylene glycol monobutyl ether, tetrahydrofurfuryl alcohol and the like.

Examples of the alkali metal hydrides include sodium borohydride, potassium boro-hydride and lithium borohydride.

In the present invention, for reducing a compound having a single functional group, it is preferred to use 0.26~1.8 moles of an alkali metal boro-hydride and 0.05~7.0 moles of a hydroxyl ether compound per 1 mole of the compound to be reduced. For reducing a compound having such plural functional groups as n functional groups (n is a positive integer), it is preferred to use n times the above amounts of an alkali metal boro-hydride and a hydroxyl ether compound.

It is possible to partially replace the hydroxyl ether compound by a lower alcohol in order to reduce the cost of the reaction solvent. Examples of the lower alcohol include methanol, ethanol and propanol. In the combined use of a hydroxyl ether compound and a lower alcohol, it is desirable to use 0.26~1.8 moles of an alkali metal boro-hydride, 0.03~3.0 moles of a hydroxyl ether compound and 0.04~5.0 moles of a lower alcohol per 1 mole of a compound to be reduced having a single functional group.

The reaction is carried out by slowly adding a hydroxyl ether compound dropwise to a mixture containing a compound to be reduced and an alkali metal borohydride, or by slowly adding both a hydroxyl ether compound and a lower alcohol dropwise to the mixture. A hydroxyl ether compound and a lower alcohol may be previously mixed together or a hydroxyl ether compound and a lower alcohol may be added dropwise to the mixture in this order. Although this reaction can be carried out at any temperature between 0° C. and 150° C., temperature between 50° C. and 150° C. is practically most desirable because the reaction proceeds faster at a higher temperature.

The method of the present invention can also be applied to the reduction of ketone compounds which have a great steric hindrance, and the corresponding alcohols can efficiently be produced on an industrial scale by the method of the present invention. For example, when bornane-3-spiro-1'-cyclopentane-2-one of the following formula (II),

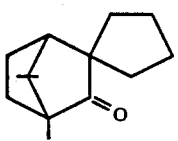
(II)

which has a carbonyl group and has a great steric hindrance, is reduced with an alkali metal boro-hydride in the presence of a hydroxyl ether compound, a pure product of bornane-3-spiro-1'-cyclopentane-2-ol of the following formula (III),

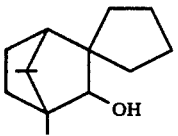
(III)

which is useful as an odorant substance, can be produced almost quantitatively.

According to the present invention, because of the use of a hydroxyl ether, it is unnecessary to use a great amount of alkali metal boro-hydride. As a result, it is possible to quantitatively reduce a target compound having a specific functional group in a short time and produce efficiently the corresponding alcohol or amine in an industrial scale.

The present invention will be further described according to the following examples.

EXAMPLE 1

A mixture consisting of 109.3 g (0.82 mole) of diethylene glycol monoethyl ether and 74.6 g (2.33 mole) of methanol was added dropwise to a mixture consisting of 28.6 g (0.76 mole) of sodium borohydride and 120 g (0.58 mole) of bornane-3-spiro-1'-cyclopentane-2-one at 60° C. over 9 hours while agitating the mixture. Subsequently, the mixture was agitated at the same temperature for 10 hours. After cooling to room temperature, the mixture was neutralized with dilute sulfuric acid and the aqueous layer was separated. The solvent was distilled off to obtain 118.2 g of a pure product of bornane-3-spiro-1'-cyclopentane-2-ol (yield: 97.6%).

Boiling point: 145° C./14 mmHg
IR(KBr tablet, $cm^{-1}$): $3700 \sim 3100(\nu_{O-H})$; $1045(\nu_{C-O})$

EXAMPLE 2

51 g (0.38 mole) of diethylene glycol monoethyl ether was added dropwise to a mixture consisting of 4.8 g (0.13 mole) of sodium borohydride and 20 g (0.1 mole) of bornane-3-spiro-1'-cyclopentane-2-one at 110° C. over 8 hours while agitating the mixture. Subsequently, the mixture was agitated at the same temperature for 12 hours. After cooling to room temperature, the mixture was neutralized with dilute sulfuric acid and the aqueous layer was separated. The solvent was distilled off to obtain 19.9 g of a pure product of bornane-3-spiro-1'-cyclopentane-2-ol (yield: 98.5%).

Boiling point: 145° C./14 mmHg
IR(KBr tablet, $cm^{-1}$): $3700 \sim 3100(\nu_{O-H})$; $1045(\nu_{C-O})$

COMPARATIVE EXAMPLE 1

50 g of bornane-3-spiro-1'-cyclopentane-2-one and 2.5 g of a copper-chromium catalyst were put in a 100 ml autoclave, and the mixture was allowed to react at 170° C. under a hydrogen pressure of 100 kg/cm² for 20 hours. After completing the reaction, the catalyst was filtered off and the gas chromatographic analysis of the resulting mixture revealed 55% conversion ratio to bornane-3-spiro-1'-cyclopentane-2-ol.

COMPARATIVE EXAMPLE 2

50 g of bornane-3-spiro-1'-cyclopentane-2-one and 2.5 g of platinum oxide used as a catalyst were put in a 100 ml autoclave, and the mixture was allowed to react at 170° C. under a hydrogen pressure of 100 kg/cm² for 17 hours. After completing the reaction, the catalyst was filtered off and the gas chromatographic analysis of the resulting mixture revealed 11% conversion ratio to bornane-3-spiro-1'-cyclopentane-2-ol.

COMPARATIVE EXAMPLE 3

50 g of bornane-3-spiro-1'-cyclopentane-2-one and 2.5 g of a copper-zinc catalyst were put in a 100 ml autoclave, and the mixture was allowed to react at 130° C. under a hydrogen pressure of 100 kg/cm² for 30 hours. After the reaction, the catalyst was filtered off and the gas chromatographic analysis of the resulting mixture revealed 72% conversion ratio to bornane-3-spiro-1'-cyclopentane-2-ol.

COMPARATIVE EXAMPLE 4

50 g of bornane-3-spiro-1'-cyclopentane-2-one and 2.5 g of ruthenium carried by activated carbon used as a catalyst (containing 50% of water) were put in a 100 ml autoclave, and the mixture was allowed to react at 135° C. under a hydrogen pressure of 100 kg/cm² for 20 hours. After completing the reaction, the catalyst was filtered off and the gas chromatographic analysis of the resulting mixture revealed 60% conversion ratio to bornane-3-spiro-1'-cyclopentane-2-ol.

COMPARATIVE EXAMPLE 5

Methanol was added dropwise to a mixture consisting of sodium borohydride, 4.6 g (0.12 mole) of bornane-3-spiro-1'-cyclopentane-2-one and tetrahydrofuran at 60° C. over one hour while agitating the mixture. Subsequently, the mixture was born at 60° C. for 10 hours.

In order to produce bornane-3-spiro-1'-cyclopentane-2-ol in a yield of 97% by the above method, 4.6 g (2.5 times the molar amount of the substrate) of sodium borohydride, 80 ml (8 times the volume of the substrate)

of tetrahydrofuran and 30 ml (3 times the volume of the substrate) of methanol were required.

EXAMPLE 3

A mixture consisting of 0.52 g (0.0039 mole) of diethylene glycol monoethyl ether and 5 ml of xylene was added dropwise to a mixture consisting of 0.65 g (0.017 mole) of sodium borohydride, 10 ml of xylene and 10 g (0.065 mole) of 4-t-butylcyclohexanone at 95° C. over 30 minutes while agitating the mixture. Subsequently, the mixture was agitated for one hour while maintaining it at 95° C. Next, after the mixture was cooled to room temperature, it was neutralized with dilute sulfuric acid. As a result, 4-t-butylcyclohexanol was quantitatively obtained.

EXAMPLE 4

8.9 g (0.066 mole) of diethylene glycole monoethyl ether was added dropwise to a mixture consisting of 1.3 g (0.034 mole) of sodium borohydride, 10 ml of xylene and 5 g (0.042 mole) of 1,2-epoxyethyl benzene at 90° C. over 1.5 hours while agitating the mixture. Subsequently, the mixture was agitated at the same temperature for 1.5 hours. After cooling to room temperature, the mixture was neutralized with dilute sulfuric acid. As a result, phenylethyl alcohol was quantitatively obtained.

EXAMPLE 5

7.5 g (0.083 mole) of ethylene glycol monoethyl ether was added dropwise to a mixture consisting of 1.6 g (0.042 mole) of sodium borohydride, 10 ml of xylene and 5 g (0.027 mole) of methyl caprate at 90° C. over two hours while agitating the mixture. Subsequently, the mixture was agitated at the same temperature for 2.5 hours. After cooling to room temperature, the mixture was neutralized with dilute sulfuric acid. As a result, n-decanol was obtained in 90% yield.

EXAMPLE 6

11.2 g (0.083 mole) of diethylene glycol monoethyl ether was added dropwise to a mixture consisting of 1.6 g (0.042 mole) of sodium borohydride, 10 ml of xylene and 5 g (0.027 mole) of methyl caprate at 90° C. over two hours while agitating the mixture. Subsequently, the mixture was agitated at the same temperature for 2.5 hours. After cooling to room temperature, the mixture was neutralized with dilute sulfuric acid. As a result, n-decanol was obtained in 97% yield.

EXAMPLE 7

13.5 g (0.083 mole) of diethylene glycol monobutyl ether was added dropwise to a mixture consisting of 1.6 g (0.042 mole) of sodium borohydride, 10 ml of xylene and 5 g (0.027 mole) of methyl caprate at 95° C. over two hours while agitating the mixture. Subsequently, the mixture was agitated at the same temperature for two hours. After cooling to room temperature, the mixture was neutralized with dilute sulfuric acid. As a result, n-decanol was obtained in 98% yield.

EXAMPLE 8

14.8 g (0.083 mole) of triethylene glycol monoethyl ether was added dropwise to a mixture consisting of 1.6 g (0.042 mole) of sodium borohydride, 10 ml of xylene and 5 g (0.027 mole) of methyl caprate at 95° C. over two hours while agitating the mixture. Subsequently, the mixture was agitated at the same temperature for 1.5 hours. After cooling to room temperature, the mixture was neutralized with dilute sulfuric acid. As a result, n-decanol was obtained in 99% yield.

EXAMPLE 9

36.2 g (0.27 mole) of diethylene glycol monoethyl ether was added dropwise to a mixture consisting of 5.1 g (0.14 mole) of sodium borohydride, 20 ml of xylene and 8 g (0.082 mole) of n-capronitrile at 110° C. over 4.5 hours while agitating the mixture. Subsequently, the mixture was agitated at the same temperature for 30 minutes. After cooling to room temperature, the mixture was neutralized with dilute sulfuric acid. As a result, hexylamine was quantitatively obtained.

EXAMPLE 10

43 g (0.32 mole) of diethylene glycol monoethyl ether was added dropwise to a mixture consisting of 6 g (0.16 mole) of sodium borohydride, 25 ml of xylene and 10 g (0.097 mole) of benznitrile at 110° C. over two hours while agitating the mixture. Subsequently, the mixture was agitated at the same temperature for 16 hours. After cooling to room temperature, the mixture was neutralized with dilute sulfuric acid. As a result, benzylamine was obtained in 74% yield and the benzynitriles remained unreactive in the proportion of 25%.

EXAMPLE 11

29 g (0.22 mole) of diethylene glycol monoethyl ether was added dropwise to a mixture consisting of 4.1 g (0.11 mole) of sodium borohydride, 40 ml of xylene and 8 g (0.066 mole) of benzamide at 110° C. over two hours while agitating the mixture. Subsequently, the mixture was agitated at the same temperature for 15 hours. After cooling to room temperature, the mixture was neutralized with dilute sulfuric acid. As a result, benzylamine was obtained in 65% yield and the benzamide remained unreactive in the portion of 34%.

EXAMPLE 12

17.9 g (0.13 mole) of diethylen glycol monoethyl ether was added dropwise to a mixture consisting of 2.6 g (0.069 mole) of sodium borohydride, 30 ml of xylene and 5 g (0.043 mole) of n-caproic acid at 90° C. over two hours while agitating the mixture. Subsequently, the mixture was agitated at the same temperature for two hours. After cooling to room temperature, the mixture was neutralized with dilute sulfuric acid. As a result, n-hexanol was quantitatively obtained.

EXAMPLE 13

18 g (0.134 mole) of diethylene glycol monoethyl ether was added dropwise to a mixture consisting of 2.5 g (0.066 mole) of sodium borohydride, 30 ml of xylene and 10 g (0.036 mole) of $\alpha,\omega$-monomethyl pentadecanoate at 110° C. over two hours while agitating the mixture. Subsequently, the mixture was agitated at the same temperature for one hour. After cooling to room temperature, the mixture was neutralized with dilute sulfuric acid. As a result, $\alpha, \omega$-pentadecanediol was obtained in 92% yield.

EXAMPLE 14

10.7 g (0.08 mole) of ethyl carbitol was added dropwise to a mixture consisting of 1.5 g (0.04 mole) of sodium borohydride and 15 ml of xylene at 120° C. for 1.5 hours. The mixture was agitated at 120° C. for one hour. A mixture consisting of 3 g (0.02 mole) of N,N- dimethyl benzamide and 10 ml of xylene was added dropwise to the mixture over 0.5 hours. Subsequently, the resulting mixture was agitated at 120° C. for 20 hours. After cooling to room temperature, the mixture was neutralized with dilute sulfuric acid. As a result, N,N-dimethylbenzylamine was obtained in 51% yield and benzyl alcohol in 47% yield, respectively.

EXAMPLE 15

29.8 g (0.222 mole) of ethyl carbitol was added dropwise to a mixture consisting of 2.8 g (0.074 mole) of sodium borohydride, 5 g (0.037 mole) of N-methyl benzamide and 25 ml of xylene at 120° C. over two hours. Subsequently, the mixture was agitated at the same temperature for 40 hours. After cooling to room temperature, the mixture was neutralized with dilute sulfuric acid. As a result, N-methyl benzylamine was obtained in 67.5% yield and benzyl alcohol in 7.7% yield, respectively. 23.6% of N-methyl benzamide was remained unreactive.

What is claimed is:

1. A process for producing an alcohol or an amine, which comprises reducing a compound having a formyl, keto, nitro, oxirane, ester, nitrile, amide, carboxyl or halogenated carboxyl group with an alkali metal borohydride in the presence of a compound having a hydroxyl group and ether linkage, wherein the compound having a hydroxyl group and ether linkage is a compound represented by formula (I):

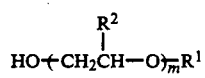

wherein $R^1$ represents an alkyl group or an alkenyl group; $R^2$ represents a hydrogen atom or an alkyl group; $R^1$ and $R^2$ may be linked together to form an alkylene group; and m represents a number of 1 to 5.

2. A process for producing bornane-3-spiro-1'-cyclopentane-2-ol which is represented by formula (III),

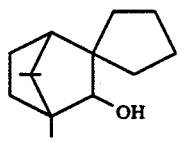

which process comprises reducing bornane-3-spiro-1'-cyclopentane-2-one represented by formula (II):

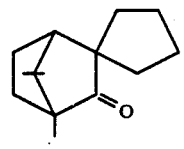

with an alkali metal boro-hydride in the presence of a compound having a hydroxyl group and ether linkage.

3. A process for producing an alcohol or an amine as set forth in claim 1, wherein the process is carried out between 0° C. and 150° C.

4. A process for producing an alcohol or an amine as set forth in claim 1, wherein said compound having a formyl, keto, nitro, oxirane, ester, nitrile, amide, carboxyl, or halogenated carboxyl group is a compound selected from the group consisting of benzaldehyde, citronellal, hydrotropaldehyde, lyral, methylheptenone, carvone, camphor, bornane-3-spiro-1'-cyclopentane-2-one, benzophenone, muscone, nitrobenzene, nitropropane, musk ambrette, styrene oxide, stilbene oxide, cyclohexene oxide, α-pinene oxide, methyl benzoate, linaryl acetate, cedryl acetate, bornyl acetate, α, ω-dimethyl pentadecanoate, cyclopentadecanolide, geranyl nitrile, citronellylnitrile, benznitrile, benzamide, N-methyl benzamide, N,N-dimethyl benzamide, caproic acid, benzoic acid, α, ω-pentadecanoic acid, phthalic anhydride, caproic acid chloride, benzoic acid chloride, and α, ω-pentadecanoic acid chloride.

5. A process for producing an alcohol as set forth in claim 1, wherein said compound having a keto group is bornane-3-spiro-1'-cyclopentane-2-one represented by formula (II):

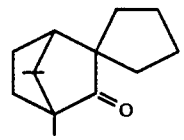

and wherein the alcohol produced is bornane-3-spiro-1'-cyclopentane-2-ol which is represented by formula (III)

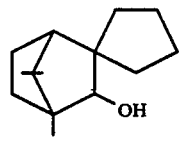

* * * * *